United States Patent [19]

Benkö et al.

[11] 4,091,206
[45] May 23, 1978

[54] QUINOXALINE-1,4-DIOXIDE DERIVATIVES

[75] Inventors: Pál Benkö; Ildikó Simonek; László Pallos; Jenö Kovács; Károly Magyar, all of Budapest, Hungary

[73] Assignee: Egyt Gyogyszervegyeszeti Gyar, Budapest, Hungary

[21] Appl. No.: 775,999

[22] Filed: Mar. 9, 1977

Related U.S. Application Data

[63] Continuation-in-part of Ser. No. 630,762, Nov. 11, 1975, abandoned.

[30] Foreign Application Priority Data

Nov. 21, 1974 Hungary .............................. EE 2278

[51] Int. Cl.² ................. C07D 241/00; C07D 401/12; C07D 405/12
[52] U.S. Cl. .................................................. 542/416
[58] Field of Search ..................... 260/240 G; 542/416

[56] References Cited

U.S. PATENT DOCUMENTS 3,493,572  2/1970  Johnson ......................... 260/250 QN
3,819,616  6/1974  Seng et al. ....................... 260/240 G Primary Examiner—Allen B. Curtis
Attorney, Agent, or Firm—Young & Thompson

[57] ABSTRACT

The invention relates to new quinoxaline-1,4-dione derivatives of the formula

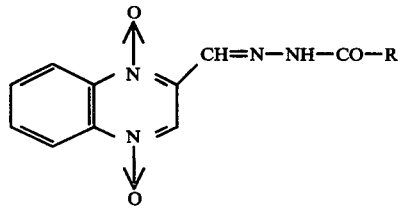

wherein R is pyridyl, 5-nitrofuryl or 1-naphthylmethyl group.

The new compounds of formula I have weight-gain increasing effects.

1 Claim, No Drawings

QUINOXALINE-1,4-DIOXIDE DERIVATIVES

This is a continuation-in-part application of application Ser. No. 630,762 filed on Nov. 11, 1975, now abandoned.

This invention relates to new quinoxaline-1,4-dioxide derivatives of the formula

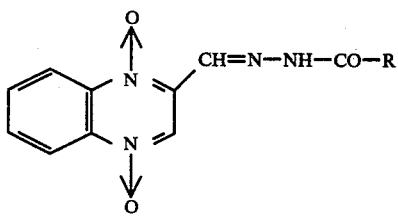

wherein R is pyridyl, 5-nitrofuryl or 1-naphthylmethyl group.

The new compounds of formula I show weight-gain increasing effects.

It is known from the British patent specifications Nos. 1,058,047 and 1,202,170 that 2-formyl-quinoxaline-1,4-dioxide-hydrazones can be prepared by reacting 2-formylquinoxaline-1,4-dioxide or its dialkyl-acetals with a $C_{1-7}$ alkanecarboxylic acid or benzoic acid hydrazides in methanol. These compounds have bactericidal and weight-gain increasing effect with animals.

The new compounds of the formula I can be prepared by (a) reacting an aldehyde of the formula

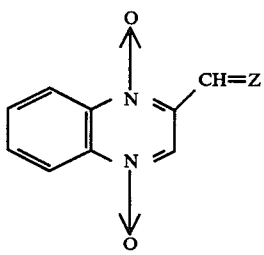

wherein Z is oxygen atom or an (O-alkyl)$_2$ group, with an acid hydrazide of the formula $$R - CO - NH - NH_2 \qquad (III)$$

wherein R is as defined above, or (b) reacting a formyl hydrazone of the formula

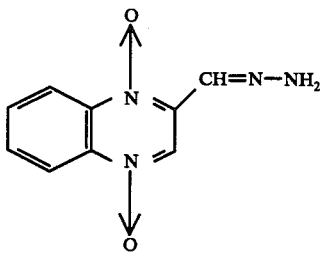

with an acid halide of the formula $$R - CO - X \qquad (V)$$

wherein R is as defined above and X is halogen.

The starting compounds of formulae II and III, that is, the 2-formyl-quinoxaline-1,4-dioxide and its diacetal as well as the carboxylic acid hydrazides can be prepared by known methods. For compounds of formula II see e.g. Ber. 84, 4771 (1951); Zh. Obshch. Him. 25, 161 (1955); British patent specification No. 1,058,047; Belgian patent specification No. 669,353. For compounds of formula III see e.g. J. Zabiczky: "The Chemistry of Amides", Chapter 10, p. 515, Interscience Publ., 1970.

Method (a) is performed preferably so that 2-formyl-quinoxaline-1,4-dioxide of formula II is reacted with a small excess of the carboxylic acid hydrazide in water, in the presence of an acid.

If 2-formyl-quinoxaline-1,4-dioxide-diacetal is reacted with a carboxylic acid hydrazide, it is preferred to carry out the reaction in a protonated medium after a short boiling. The protonated medium can be ensured by the addition of an acid. Mainly a mineral acid, such as hydrochloric, sulfuric and phosphoric acid, can be used as acid, but ptoluenesulfonic acid can be used as well for this purpose.

Any solvent which does not react with the reactants or the products and is miscible with the acid employed as catalyst can be used as reaction medium. Generally it is preferred to carry out the reaction in water.

Method (b) is performed preferably so that the 2-formyl-quinoxaline-1,4-dioxide-hydrazone is reacted with the carboxylic acid halide in such a molar ration that the acid formed in the reaction be bound by the basic reactant.

According to an other preferred embodiment of process variant (b) the reaction can be carried out in the presence of an acid-binding agent, such as triethyl amine or sodium hydrocarbonate.

A further preferred embodiment of process variant (a) which can preferably be applied when producing the compounds of formula I in a continuous bulk process consists in reacting the carboxylic acid hydrazide after its preparation without isolation, that is, in the reaction mixture for preparing same, with the 2-formyl-quinoxaline-1,4-dioxide or the acetal of the latter compound. Thereby savings in labour and apparatus can be achieved in relation to the batchwise method of preparation.

The new compounds according to the invention can be admixed with fodder as weight-gain increasing agents.

When utilized as fodder additives, the new compounds according to the invention increase the weight gain and fodder utilization of pigs. The weight gain increasing effect of the compounds was tested on pigs as follows:

The animals were fed under the same conditions with fodders of the same amount and composition. In the test groups the animals received a fodder admixed with 50 mg./kg. of the compound to be tested, whereas no additive was admixed with the fodder in the control group.

The weight gain was measured daily, and the feeding coefficient (amount of consumed fodder resulting in a weight gain of 1 kg.) was calculated. The percentage daily weight gain was calculated by the formula $$\frac{\text{daily weight gain in the test group} \times 100}{\text{daily weight gain in the control group}}$$

Since the rate of weight gain increasing effect depends on both the feeding coefficient and the percentage daily weight gain, and because of the actual fodder consumption and the time required to reach the slaughter weight are the important factors of economical animal husbandry, an index characteristic of the rate of weight gain increase was calculated from the above data by the equation $$\text{fodder utilization factor} = \frac{\text{percentage daily weight gain}}{\text{feeding coefficient}}$$

The higher is the fodder utilization factor the more economic is the pig-breeding.

The fodder utilization factors determined for the compounds according to the invention, furthermore the oral toxicity data of the novel compounds measured on mice are listed in Table 1. For the sake of comparison the respective data of some known compounds structurally related to those of formula I are also given.

Table 1

| Meaning of R in the formula I compound | Fodder utilization factor | Toxicity $LD_{50}$ mg./kg. |
| --- | --- | --- |
| methoxy[1] | 66 | 4000 |
| hexyl[2] | 53 | 4000 |
| phenyl[3] | 66 | 4000 |
| 4-pyridyl | 91 | 12000 |
| 5-nitrofuryl | 91 | 14000 |
| 1-napthylmethyl | 93.5 | 13000 |
| Control | 50 | — |

Remarks:
[1]2-(Methoxycarbonyl-hydrazono-formyl)-quinoxaline-1,4-dioxide described in the U.S. Pat. spec. No. 3,493,572.
[2]2-(Hexylcarbonyl-hydrazono-formyl)-quinoxaline-1,4-dioxide described in the British Pat. spec. No. 1,058,572.
[3]2-(Benzoyl-hydrazono-formyl)-quinoxaline-1,4-dioxide described in the British Pat. spec. No. 1,058,572.

The data of Table 1 clearly demonstrate that the compounds according to the invention ensure far higher fodder utilization factors than the known ones. As far as the known compounds are concerned, their fodder utilization factors are only slightly higher than that observed in the control group. Moreover, the new compounds according to the invention are far less toxic than the known ones. This very low toxicity is of particular importance when the animals are treated continuously with fodder additives.

The invention is elucidated in detail by the aid of the following non-limiting Examples.

EXAMPLE 1

2-(1'-Naphthyl-acetyl)-hydrazono-formyl-quinoxaline-1,4-dioxide 9.5 g. (0.05 moles) of 2-formyl-quinoxaline-1,4-dioxide are dissolved in 100 ml. of water containing 0.5 ml. of concentrated hydrochloric acid and then 10.0 g. (0.05 moles) of 1-naphthyl-acetic acid hydrazide are added to the solution. After stirring for 3 hours at room temperature, the suspension is filtered and the precipitate is washed with water and ethanol. In this way 16.2 g. (87%) of the title compound are obtained with a melting point of 246°—247° C.

EXAMPLE 2

2-(Nicotinoyl)-hydrazono-formyl-quinoxaline-1,4-dioxide 7.55 g. (0.05 moles) of nicotinic acid ethyl ester are dissolved in 60 ml. of ethanol, then 2.6 g. (0.05 moles) of 96% hydrazine hydrate are dropped to the obtained solution. The reaction mixture is boiled for 2 hours, then the warm solution of 9.5 g. (0.05 moles) of 2-formyl-quinoxaline-1,4-dioxide and 1 ml. of concentrated hydrochloric acid in 140 ml. of methanol is dropped to it. The reaction mixture is allowed to cool to room temperature, then it is stirred for two hours at this temperature. The separated crystals are filtered and washed with methanol. In this way 13.2 g. (85.4%) of the title product are obtained with a melting point of 279° C.

EXAMPLE 3

2-(Isonicotinoyl)-hydrazono-formyl-quinoxaline-1,4-dioxide 75 ml. of an aqueous suspension of 11.8 g. (0.05 moles) of 2-formyl-quinoxaline-1,4-dioxide dimethylacetal and 4 ml. of concentrated hydrochloric acid are boiled for about ten minutes, whereafter 50 ml. of a warm aqueous suspension of 6.85 g. (0.05 moles) of isonicotinic acid hydrazide are added. The reaction mixture is allowed to cool to room temperature, then it is stirred for three hours. The resulting precipitate is filtered, washed with water and ethanol, and dried. 14.4 g. (93.2%) of the title product with a melting point of 268° C are obtained.

EXAMPLE 4

2-(5'-Nitro-2'-furanoyl)-hydrazono-formyl-quinoxaline-1,4-dioxide 4 ml. of concentrated aqueous hydrochloric acid are added to a suspension of 11.8 g. (0.05 moles) of 2-formyl-quinoxaline-1,4-dioxide-dimethylacetal in 75 ml. of water. The mixture is boiled for 10 minutes, thereafter a suspension of 8.6 g. (0.05 moles) of 5-nitrofurane-2-carboxylic acid hydrazide in 50 ml. of warm water is added. The reaction mixture is allowed to cool to room temperature, then it is stirred for 3 hours. The separated product is filtered off and washed with water and ethanol. The title product, melting at 265° C, is obtained with a yield of 82.6%.

What we claim is:
1. A quinoxaline-1,4-dioxide derivative of the formula

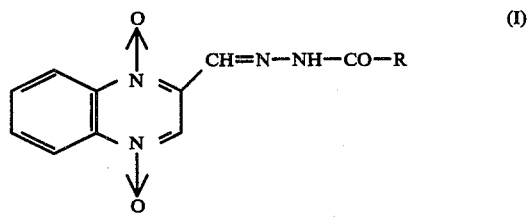

wherein R is pyridyl, 5-nitrofuryl or 1-naphthylmethyl group.

* * * * *